(12) United States Patent
Sherman

(10) Patent No.: US 9,242,093 B1
(45) Date of Patent: Jan. 26, 2016

(54) SPECIALTY APPAREL TO BE USED TO CONCEAL A HEARING DEVICE AND ITS WIRES TO HELP PROTECT AGAINST ENTANGLEMENT, DISLODGEMENT AND SNAGS

(71) Applicant: Eric Sherman, Tarzana, CA (US)

(72) Inventor: Eric Sherman, Tarzana, CA (US)

(*) Notice: Subject to any disclaimer, the term of this patent is extended or adjusted under 35 U.S.C. 154(b) by 0 days.

(21) Appl. No.: 14/149,025

(22) Filed: Jan. 7, 2014

(51) Int. Cl.
  A61N 1/00 (2006.01)
  A61N 1/36 (2006.01)

(52) U.S. Cl.
  CPC .................. A61N 1/36032 (2013.01)

(58) Field of Classification Search
  CPC ... A41D 13/1281; A41D 1/002; A41D 1/005; A41D 13/0012; A41D 27/20
  See application file for complete search history.

(56) References Cited

U.S. PATENT DOCUMENTS

| | | | |
|---|---|---|---|
| 6,563,424 B1 * | 5/2003 | Kaario | 340/572.1 |
| 7,364,491 B2 | 4/2008 | Updyke | |
| 7,519,192 B1 | 4/2009 | Laycock et al. | |
| 7,673,348 B2 | 3/2010 | Williams | |
| 8,107,653 B2 | 1/2012 | Wolfe | |
| 8,411,891 B2 | 4/2013 | Del Prete | |
| D688,849 S | 9/2013 | Kochling | |
| 2003/0074712 A1 | 4/2003 | Liao | |
| 2003/0144039 A1 | 7/2003 | Lin | |
| 2006/0099864 A1 | 5/2006 | Crumrine | |
| 2006/0239486 A1 * | 10/2006 | Eves | 381/334 |
| 2006/0280322 A1 | 12/2006 | Abe | |
| 2007/0245444 A1 * | 10/2007 | Brink | 2/69 |
| 2008/0009918 A1 * | 1/2008 | Zierhofer et al. | 607/57 |
| 2008/0184459 A1 * | 8/2008 | Barnes | 2/249 |
| 2009/0094725 A1 * | 4/2009 | Smith et al. | 2/69 |
| 2009/0139013 A1 * | 6/2009 | Sapowycz et al. | 2/247 |
| 2010/0071110 A1 * | 3/2010 | Stevens | 2/69 |
| 2011/0185471 A1 * | 8/2011 | Buczkowski et al. | 2/84 |
| 2012/0060260 A1 | 3/2012 | Kochling | |
| 2012/0185999 A1 * | 7/2012 | Raviv | 2/247 |
| 2013/0044908 A1 | 2/2013 | Gotlieb | |
| 2014/0068832 A1 * | 3/2014 | Jordan et al. | 2/69 |
| 2014/0275736 A1 * | 9/2014 | Ruppersberg et al. | 600/25 |

FOREIGN PATENT DOCUMENTS

CN 201107863 Y 8/2008

* cited by examiner

Primary Examiner — Robert N Wieland
(74) Attorney, Agent, or Firm — Thomas I. Rozsa

(57) ABSTRACT

A specialty garment accessory to be used with a hearing improvement device having a pair of external magnetic microphones magnetically attached to opposite sides of a person's head and each external magnetic microphone having a power cord extending from a respective external microphone to a respective driving unit/sound process, each sound and power cord extending through a respective loop in the specialty garment accessory and connected to its driving unit/sound processor which are respectively retained in a respective pocket on a sleeve of the specialty garment accessory and a respective cover which covers each respective pocket so that the sound and power cords are mostly concealed within the specialty garment accessory and the driving unit/sound processors are concealed within a respective pocket.

9 Claims, 9 Drawing Sheets

SPECIALTY APPAREL TO BE USED TO CONCEAL A HEARING DEVICE AND ITS WIRES TO HELP PROTECT AGAINST ENTANGLEMENT, DISLODGEMENT AND SNAGS

BACKGROUND OF THE INVENTION

1. Field of the Invention

The invention relates to the field of devices used to restore hearing loss and in particular, to the field of garments to be worn to at least partially conceal the exterior portion of the device and helps prevent elements of the device from entanglement, dislodgment and snags.

This invention involves a specialty apparel accessory to be used with an innovation which has already been developed. The human ear has an outer drum comprising an ear canal which leads to the eardrum. The middle ear has middle ear bones. The inner ear has cochlea and the auditory nerve. Sound enters the ear canal and travels to the eardrum. The sound waves cause the eardrum to vibrate sending the bones in the middle ear into motion. Tiny hairs inside the inner ear (cochlea) convert this motion into electric impulses/signals. These impulses/signals go up to the hearing (auditory) nerve to the brain. The brain interprets the impulses/signals as sound and gives meaning to the information. One device that helps treat hearing loss is a cochlear implant.

One disability that people face is that they have a hearing loss either through birth or through an accident where the middle ear is damaged and therefore they cannot hear. People suffering from hearing loss can benefit from cochlear implants. Cochlear implants consist of both internal and external devices where a device is implanted within the cochlea on either side of the skull, bypassing the middle ear to stimulate the auditory nerve. On the outside of the person's head are magnetic microphones which are magnetically attached to an internal implant. The external microphones are connected to sound cords/wires that extend to an external driving unit/sound processor. Each driving unit/sound processor is programmed specifically to its respective internal processor implanted in the cochlea. A specific driving unit/sound processor can not be interchanged between each side of the head of the same person or with another person's implant. These external elements are expensive and unique to the individual cochlea and the design of their respective manufacturers. Therefore, they must be portable. The area of the present invention is to retain and conceal as much of the external portion of the hearing restoration device as possible to help prevent entanglement, dislodgement or snags, and be compatible with different manufacturer designs.

In some devices, the driving unit and the sound processor unit are together in a combined unit. In other devices, the sound processor is a separate unit retained behind the individual's ear and is hard wired to a separate driving unit.

Existing accessories today that hold the eternal portions of the device do not adequately retain and conceal the external driving unit/sound processor and its wires to help protect against inadvertent entanglements, dislodgement and snags particularly during physical activity such as swimming, bike riding, running etc.

2. Description of the Prior Art

The following 15 patents and published patent applications are the closest prior art to the present invention.

1. United States Published Patent Application No. 2003/0074712 to Sheng Hsin Liao on Apr. 24, 2003 for "Clothes Having Detachable Hidden Communication Wire" (hereafter the "Liao Published Patent Application");

2. United States Published Patent Application No. 2003/0144039 to Yung Fang Lin on Jul. 31, 2003 for "Communication Cord Pathway Concealed Clothes" (hereafter the "Lin Published Patent Application");

3. United States Published Patent Application No. 2006/0099864 to Scott Crumine et al. on May 11, 2006 for "Life Vest With Integrated Audio Device and Method of Use" (hereafter the "Crumine Published Patent Application");

4. United States Published Patent Application No. 2006/0280322 to Kaho Abe on Dec. 14, 2006 for "Discreet Interface System" (hereafter the "Abe Published Patent Application");

5. United States Published Patent Application No. 2007/0245444 to William Brink on Oct. 25, 2007 for "Specialty Clothing Designed To Hold Portable Electronic Devices" (hereafter the "Brink Published Patent Application");

6. U.S. Pat. No. 7,364,491 issued to Lauren Grace Updyke on Apr. 29, 2008 for "Sports Bra with Secure Pocket and Electronic Device Cord Securing Opening and Loop" (hereafter the "Updyke Patent");

7. U.S. Pat. No. 7,519,192 issued to Logan Laycock et al. on Apr. 14, 2009 for "Wired Clothing and Earphones" (hereafter the "Laycock Patent");

8. United States Published Patent Application No. 2009/0094725 to Stephen Smith et al. on Apr. 16, 2009 for "Clothing For Use With Personal Electronic Listening Devices" (hereafter the "Smith Published Patent Application");

9. U.S. Pat. No. 7,673,348 issued to Herman Williams on Mar. 9, 2010 for "User Wearable Wire Control System" (hereafter the "Williams Patent");

10. U.S. Pat. No. 8,107,653 issued to James Wolfe on Jan. 31, 2012 for "Garment With Built-in Audio Source Wiring" (hereafter the "Wolfe Patent");

11. United States Published Patent Application No. 2012/0060260 to Edmund T. Kochling on Mar. 15, 2012 for "Pocketed Garment" (hereafter the "Kochling Published Patent Application");

12. United States Published Patent Application No. 2013/0044908 to Lawrence Mark Gottlieb on Feb. 21, 2013 for "Apparel With Built-In Headphone Extension Wire Device" (hereafter the "Gottlieb Published Patent Application");

13. U.S. Pat. No. 8,411,891 issued to Anontino Del Prete on Apr. 2, 2013 for "Garment With Integrated Earphones" (hereafter the "Del Prete Patent");

14. U.S. Design Pat. No. D688,849 issued to Edmund T. Kochling on Sep. 3, 2013 for "Shirt with Pocket" (hereafter the "Kochling Design Patent");

15. Chinese Patent No. CN201107863Y issued to Jiang Tao and assigned to Sichuan Micro-DSP Digital Technology Co., Ltd. on Aug. 27, 2008 for "Hearing Aid Concealed in Clothes" (hereafter the "Tao Chinese Patent").

The Liao Published Patent Application discloses the concept of having a communication wire that is protected by being placed in longitudinal channels within a garment such as a jacket or shirt. The shirt or jacket has detachable hidden communication wires.

The Lin Published Patent Application discloses the concept of a communication device concealed within clothing. The patent application discloses:

"Communication cord pathway concealed clothes conceals a communication pathway along a sleeve or other seamed edges of clothes with both ends opened near the user's side and pocket where an earphone and a microphone is connected to the upper end of a communication cord laid in the pathway; while a cellular phone of various brands or other electronic device is connected to the lower end of said cord thereby forming a communication circuit. The user may use the cellular phone or the like conveniently and securely without the fear of the cord to twine around things nearby causing the cellular phone to drop down on the ground."

The Crumrine Published Patent Application discloses:

"A life vest is adapted to retain or hold a waterproof audio playback device so that a wearer of the life vest when engaging in water-related activities can listen to audio playback. The life vest can utilize pockets or device holders to integrate the audio playback device, and can also integrate one or more lead wires of the audio playback device into the vest."

The Abe Published Patent Application discloses:

"The present invention relates generally to a system for interfacing electronic devices with at least one garment. In particular, the invention pertains to a washable system for interfacing electronic devices with at least one garment wherein the system includes at least one connector, a conductive material, and at least one user interface."

The Brink Published Patent Application discloses specialty clothing designed to hold portable electronic devices such as a radio, iPod player, etc. In general, the patent application discloses:

"The present invention relates generally to clothing and more specifically to garments designed and customized to securely restrain portable electronic devices. The clothing has at least one pocket that may be specifically sized to a known electronic device shape or may be adjustable to devices of various shapes to provide a snug, secure and, safe environment for the electronic device and any electronic device accessories. The pocket also may contain a channel leading from the pocket to one or more openings near the top of the garment to allow for access to headphones. Further, channels may lead from one pocket to one or more additional pockets to allow for interconnectivity between an electronic device and an electronic device accessory. The internal channels may also contain a strap to secure wires associated with a portable electronic device or accessory in place."

The Updyke Patent discloses:

"A combination sports bra and secure pocket garment has a front mounted three section pocket with a single zipper closure. A cord hole in the pocket and a cord loop on the bra enables a cord to be retained from an electronic device in the closed pocket to a headset on the wearer."

The Laycock Patent discloses the following key features:

"The present invention provides for various embodiments of a combined garment and earphones. The combined garment and earphones includes a garment having a series of elongate internal passageways. Partially enclosed within the series of elongate internal passageways is a conductive wire assembly. The conductive wire assembly includes a first length of wire leading to at least one earpiece having a transducer for emitting audio into a user's ear, and a second length of wire leading to a connector configured to be communicatively coupled to an audio device. Finally, a retractable dial is coupled to the garment, wherein a portion of the conductive wire assembly travels through the retractable dial. The retractable dial is configured to selectively retract at least a portion of the first end of the conductive wire assembly."

The Smith Published Patent Application discloses:

"An article of clothing for supporting a personal electronic listening device comprised off at least one pocket on the clothing, each pocket having at least one pocket aperture to allow an earpiece cord of the personal electronic listening device to pass from inside the pocket to outside of the clothing, and at least one clothing aperture on the clothing, each clothing aperture allowing the earpiece cord to pass from outside to inside the clothing and to on or near the wearer's head. The pocket can further include a cover flap to temporarily close the opening and the cover flap can further include a fastening member to temporarily secure the cover flap to the body of the pocket."

The Williams Patent discloses a user wearable wire control system. Specifically, the patent discloses:

"A user wearable wire control system and associated processes that can be utilized to control a dangling wire along a user's body. The user wearable wire control system includes a first layer and second layer that are configured to form a sleeve with a hollow portion disposed therein. The sleeve is adapted to encase a least a portion of a wire. The sleeve includes a first aperture at a first end portion configured to allow at least a portion of the wire to enter the sleeve and a second aperture at a second end portion configured to allow at least a portion of the wire to exit the sleeve. As such, a wire that would otherwise dangle loosely along the body of a user may be at least partially encased in the sleeve and may reduce the danger and/or inconvenience of a dangling wire."

The Wolfe Patent discloses a garment with built-in audio source wiring. Specifically, the patent discloses:

"An audio source device may be used with a garment such as a hooded garment by passing the audio wires into a channel in the hood and having them exit the hood inside hollow lanyards with earbuds at the ends. A means to fix the wires and the lanyards to each other inside the hood is shown; and a means is shown to prevent lateral movement inside the hood."

The Kochling Published Patent Application discloses a pocketed garment. Specifically, the patent discloses:

"A pocketed garment dimensioned to cover at least a portion of a torso of a person. According to one embodiment, the garment is a shirt, and a pocket is positioned on the rear exterior of the shirt. The pocket includes a first opening for insertion of a portable entertainment device into the pocket. The pocket also includes a second opening through which headphone wires, connected to the portable entertainment device, may be passed."

The Gotlieb Published Patent Application discloses:

"The present invention provides for the embodiments for a combined apparel and conductive extension wire assembly to bridge connectivity between a portable audio listening devices and transducers that emit audio sounds. The combined garment and extension wire assembly comprises of a garment (such as a shirt, jacket, cap, etc.) having an electrical wire with a connector on one end positioned within the interior of a garment pocket for conductive connectivity to the audio output of a portable listening device held within said pocket. The extension wire assembly shall channel through the interior of the garment through passageways or within garment seams, extending to garment apertures wherein a left and right channel wire shall respectively pass through and exit the apparel fabric having each wire ending with a connector enabling further conductive connectivity respectively to left and right channel transducers emitting audio sounds."

The Del Prete Patent discloses a garment with integrated earphones. Specifically, the patent discloses:

"The invention is a garment with an integrated earphone, headset, and wire. The wire allows an audio signal to travel from an electronic device at one end of the wire to the earphone or earphones, and/or a microphone at the other end of the wire. The wire, or wires, is preferably permanently sewn into the seams of the garment. The earphone may be retractable and/or kept in a small pocket near the collar of the garment to limit the movement of the earphone when it is not being actively used. The integrated earphone and microphone are preferably machine washable and dryable along with the garment with which they are integrated."

The Kochling Design Patent discloses the shape or ornamental features of the device which is disclosed in the published application to Kochling 2012/0060260.

The Tao Chinese Patent discloses:

"The utility model provides a hearing aid which is hidden in a coat and relates to the hearing auxiliary equipment technology field. The hearing aid includes a signal collector, a signal transmission line, a hearing aid processor and a headphone. The signal collector is arranged on the upper part of the coat. The hearing aid processor is arranged on the coat and is communicated with the signal collector through the signal transmission line. The hearing aid is simultaneously provided with the functions of the hearing aid and the coat and is especially applicable to the aged and the disabled with hearing loss and inconvenient action."

SUMMARY OF THE INVENTION

The invention involves a specialty garment accessory to be used with an innovation which has already been developed. One disability that some people face is that they have a hearing loss either through birth or through an accident and therefore, they cannot hear. An innovation was created where an implant was inserted into the cochlea on either side of the skull, bypassing the middle ear and stimulating the auditory nerve, so that the person can hear. On the outside of the person's head are magnetic microphones on either side of a person's head which are magnetically attached to an internal hearing processing device that is retained within the skull. There is one on either side of the head for each ear. Wires then extend from each magnetic microphone to a driving unit/sound processor which is retained in a pocket.

The main object of the present invention is to retain and conceal as much of the exposed portion of the external components of the cochlear implant device to prevent against entanglements, dislodgment and snags.

The innovation of the present invention is having a specialty garment accessory wherein wires that extend from the magnetic microphone to the driving unit/sound processor can be partially concealed in the garment so that they are not inadvertently pulled out or damaged while the person is engaged in an activity such as swimming. Specifically, the specialty garment accessory is a shirt with pockets to hold external driving unit/sound processors (driving unit and driver unit are used interchangeably). The pockets contain an elastic band across the interior of the pocket. Placing the driving unit/sound processor within the pocket and clipping it to the elastic band secures and conceals it within the pocket. There is an opening within the backside of the pocket that allows the wire to pass through the inside of the shirt up through the respective loop in the collar and then connects to the magnetic microphone which magnetically connects to the internal portion of the implant portion of the device. The collar loop is used to guide the wire internally through the shirt between the magnetic microphone and driver unit/sound processor to reduce possible entanglement and allows for easy location of a magnetic microphone if dislodged. The same pocket elements are provided on the opposite side of the shirt should a second implant device be utilized. This is how the specialty garment accessory uniquely retains and conceals the external portions of the hearing devices. In this way, the probability of the wires inadvertently being pulled out or damaged while the person is engaged in an activity such as swimming will be significantly reduced.

In an alternative variation of the prior art, the microphone is wired to a sound processor which is retained behind the wearer's ear. Since this is a very small distance, concealment of the wire is not necessary. The sound processor is then hard wired to the driving unit which is contained within the pocket. The difference between this variation and the variation discussed above is that in the prior variation the sound processor and driving unit were in one combined unit retained within the garment and hard wired to the magnetic microphone; whereas, in the alternative variation, the magnetic microphone is hard wired to the sound processor retained behind the individual's ear and then the sound processor is hard wired to the driving unit retained within a garment.

Therefore, the innovation is to have the wires from the magnetic microphones extend through a respective loop within the shirt adjacent the collar with the wires on both sides extending along the interior of the shirt on either side and then extend into a respective pocket retained on the outside sleeve of the shirt where the driving unit/sound processor is retained with a clip attached to a transverse elastic band within a respective pocket which is then covered with a covering section so that each driver unit/sound processor is also concealed and protected and the wires are not exposed except for the brief location between the top collar of the shirt and the person's head to enable the person to actively engage in activities such as sports or swimming and at the same time enable a person to hear because of this new innovation. In this way, the wires will not inadvertently be pulled out or damaged while the person is engaged in an activity such as swimming.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF EMBODIMENTS OF THE PRESENT INVENTION

Figure 1:
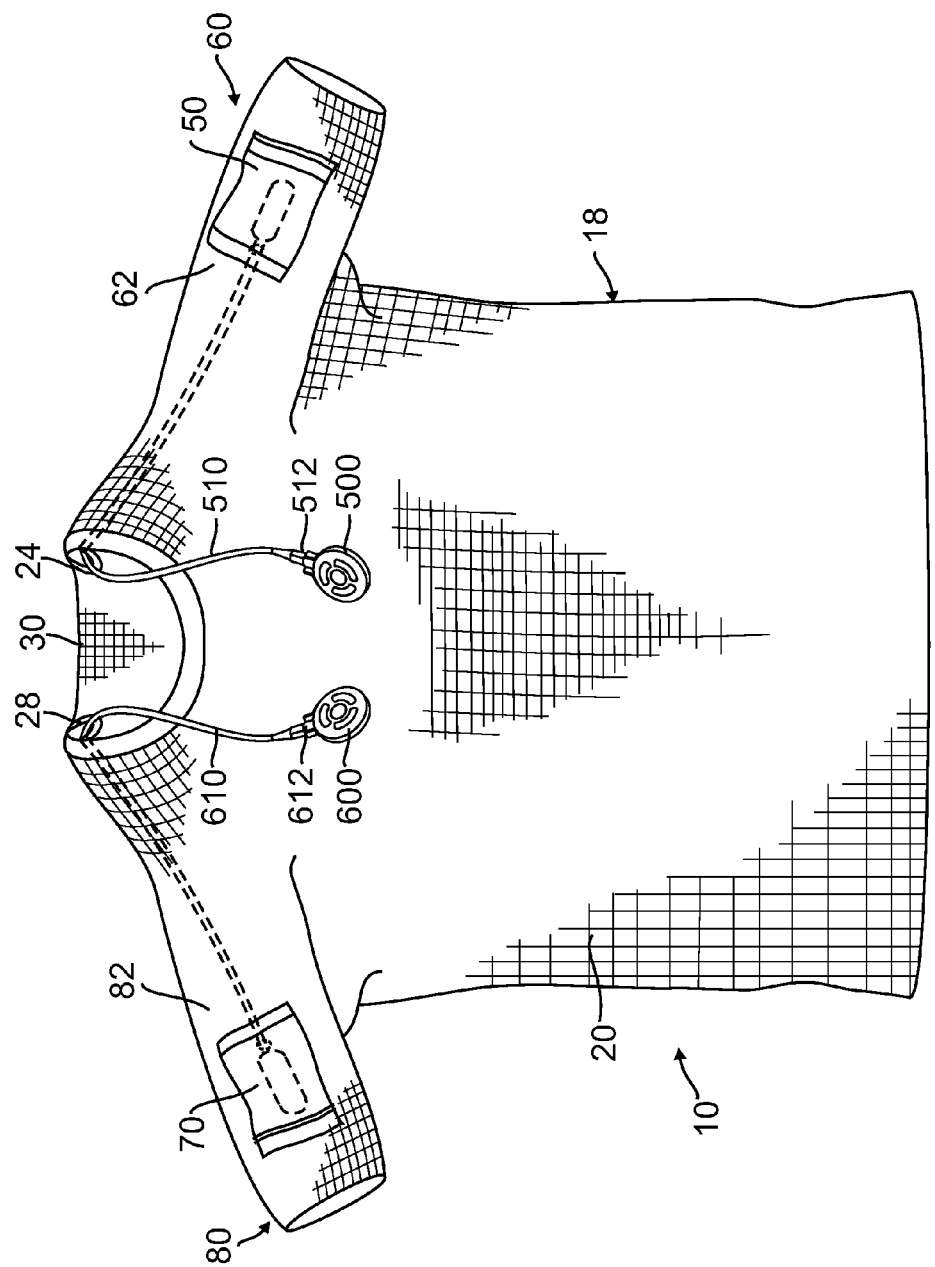
FIG. 1 is a front elevational view of an example of the present invention specialty garment accessory retaining the wires from a pair of magnetic microphones respectively wired to a respective driver unit/sound processor retained in a respective pocket in opposite sleeves on the specialty garment accessory.

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

The invention involves an improvement to be used with an innovation which has already been developed, namely the cochlear implant. One disability that some people face is that they have a hearing loss either through birth or through an accident where their middle ear is damaged and therefore, they cannot hear. An innovation called a cochlear implant has been created where an implant has been placed so that it is implanted on either side of the skull and goes to the inner ear bypassing the middle ear to stimulate the auditory nerve so that the person can hear. Information on the cochlear implant can be found on the National Institute of Deafness and other Communications Disorders website http://www/nih.gov/health/hearing/pages/coch.aspx.

The present invention is intended to be used with other types of devices and not strictly and solely with the cochlear implant. The key is that the external portion of the device will have wires extending from the device to a driving unit. However, while the cochlear implant has a portion which is implanted within the human skull as will be set forth below, in general, the device can be referred to as a hearing restoration device. This device includes the portion that is implanted in the human skull or with the anticipation of technological improvements, may not have to be implanted in the human skull. The key feature of any hearing restoration device is to restore hearing or sound to an individual. (Not all hearing devices stimulate the auditory nerve some amplify sound or send impulses directly into the brain.) Therefore, the key feature of the hearing restoration device with which the present invention is used, has an external driving unit/sound processor which turns sound into a neural signal and transfers that signal to an implanted sound processing unit within in the skull. It bypasses the middle ear to stimulate the auditory nerve which sends signals to the brain for hearing. Therefore, in the broader claims this portion of the invention will be referred to as a hearing restoration device. It is to be read as to include devices that are implanted within the skull to bypass the middle ear and stimulate the auditory nerve. In addition, the present invention can also be used with any other device which may also be affixed to the outer portion of the skull that sends messages to the brain to restore hearing. These other devices might bypass the auditory nerve to a wireless communication, implant directly into the brain, or amplify sound on the ear. These other devices may have their attachment mechanisms on the outside of the head and other external features that would be used with the specialty garment accessory of the present invention.

Also, as will be described in the succeeding paragraphs, the magnetic microphones described as numbers 500 and 600, referenced in FIG. 1 can also be interpreted to mean microphones, or headpieces that transmit signals for hearing. These microphones or headpieces are not necessarily magnetically attached, but are attached in some other way to a variation of the internal hearing restoration device. Instead of necessarily defining it as a magnetic microphone, this portion of the hearing restoration device can also be described as a first external hearing component and a second external hearing component, each of which are removably attached to respective exterior locations on opposite sides of a person's head respectively aligned with a respective hearing restoration device. Therefore, in the event there is an improvement but it still requires wires going from the external device into the driver unit/sound processor which is also external (including the variation where the restoration device is affixed to a sound processor retained behind the person's ear and then the sound processor is hard wired to the driver unit which is retained within the garment or alternatively as discussed above, the sound processor and driver are in one unit retained in the garment and the restoration device is hard wired directly from the hearing restoration device to the sound processor/driver contained in one unit), such device is within the spirit and scope of the present invention which would also cover any improvement in the prior art where the hearing restoration device does perform the function of bypassing the middle ear to stimulate the auditory nerve so the brain picks up the appropriate sound messages but has an external device which is affixed to the outer portion of the head but does not necessarily have to be magnetically affixed.

In the detailed descriptions following the first embodiment will be described in detail but it will be appreciated that these additional embodiments are also within the spirit and scope of the present invention.

Figure 2:
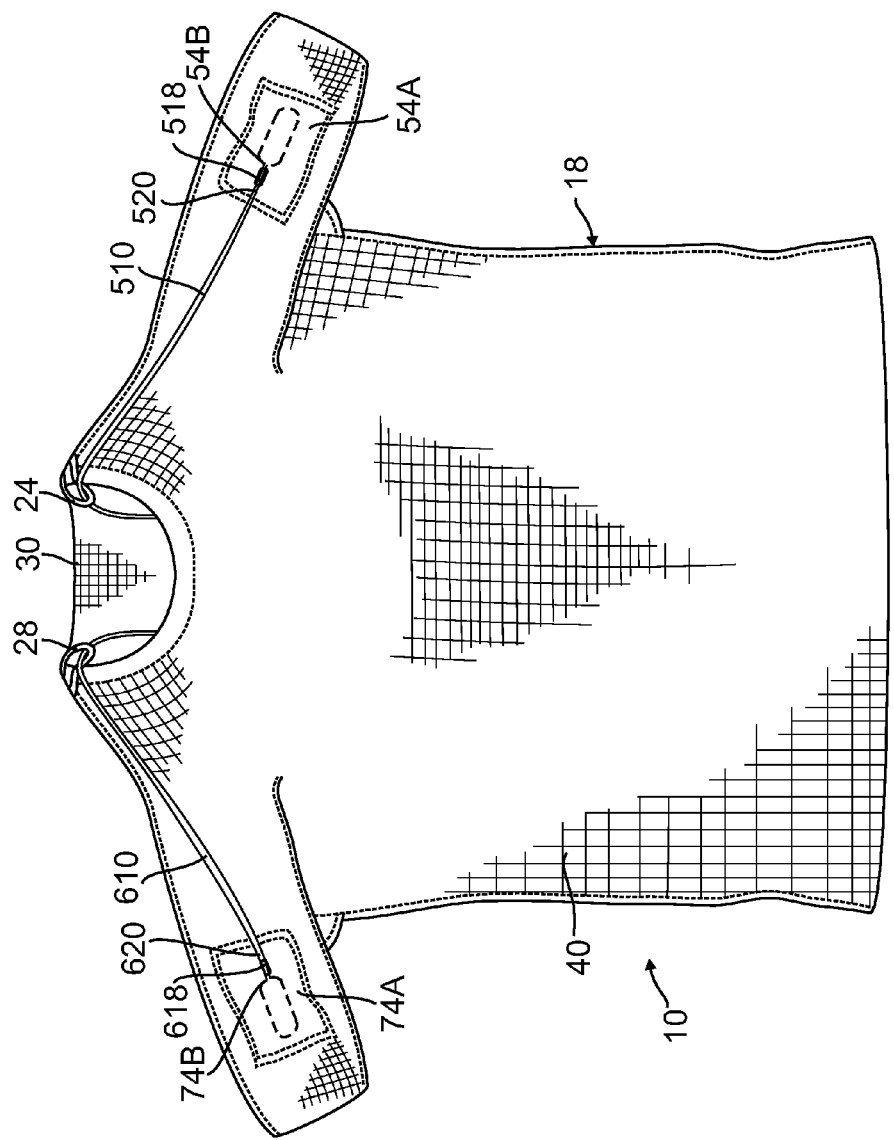
FIG. 2 is a front elevational view of the specialty garment accessory and portions of an ear implant device to restore hearing as illustrated in FIG. 1, with the specialty garment accessory turned inside out.
Figure 3:
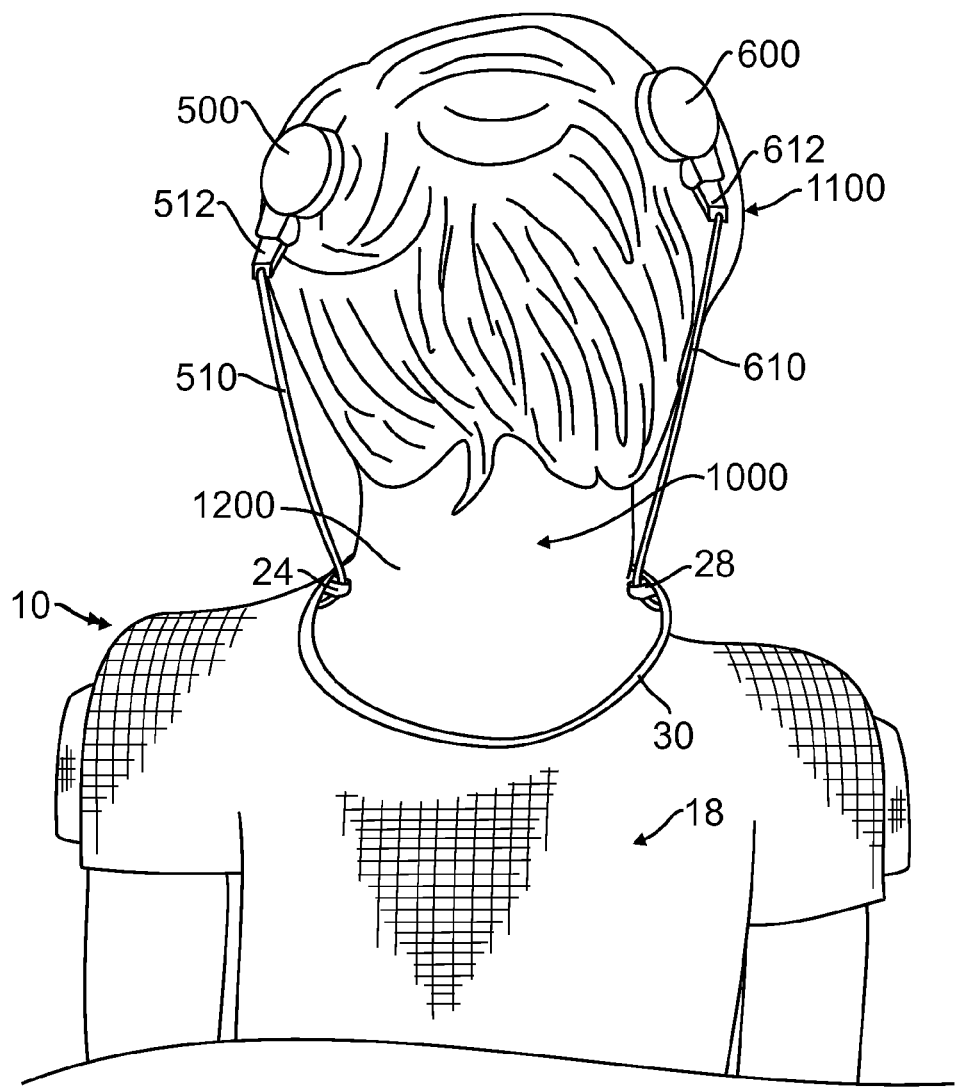
FIG. 3 is a rear elevational view of an example of the present invention specialty garment accessory with a pair of magnetic microphones retained on opposite sides of a person's head and wires from the magnetic microphones respectively extending through a loop on opposite interior sides of the specialty garment accessory and adjacent the top open collar of the specialty garment accessory.
Figure 4:
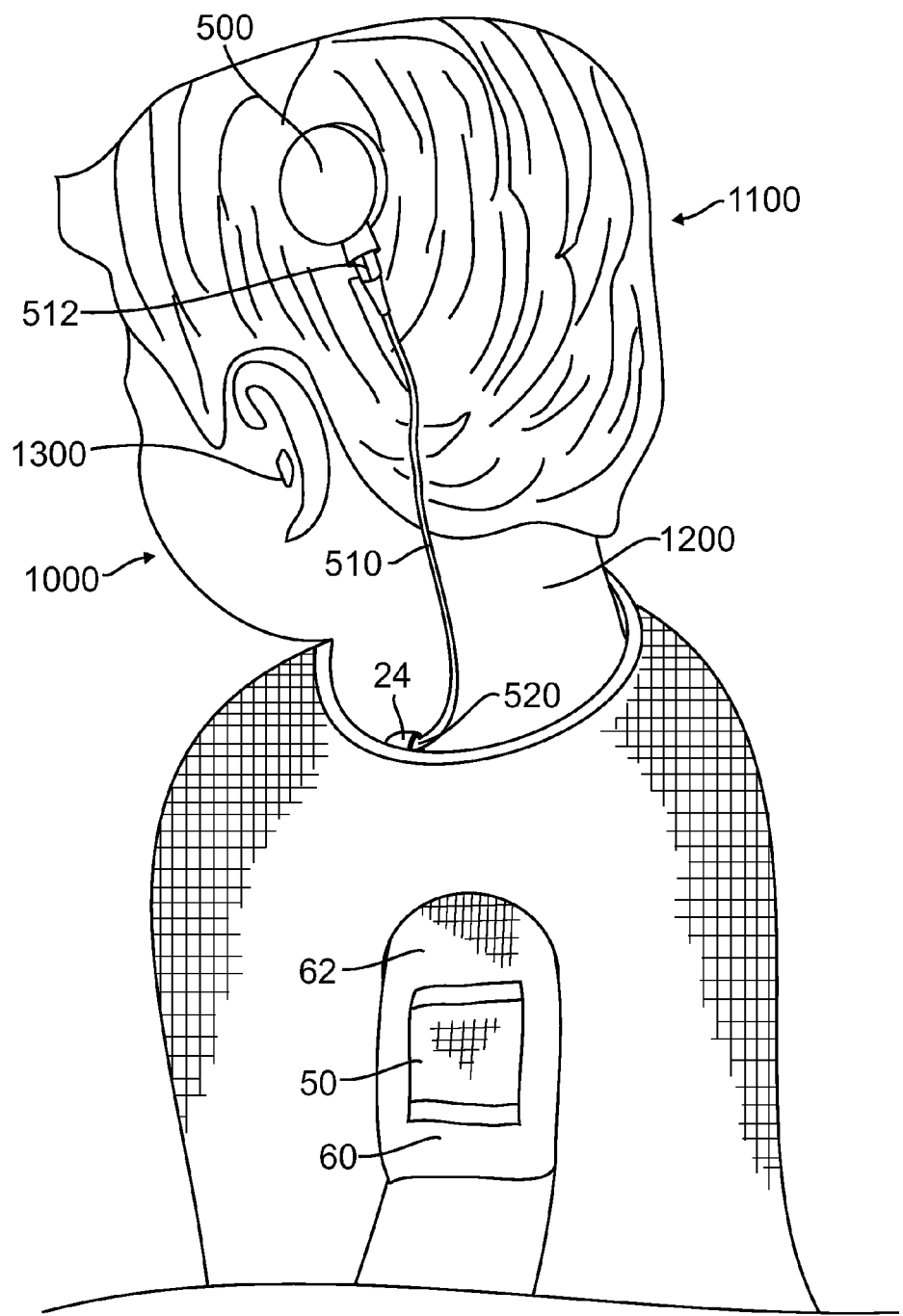
FIG. 4 is a side elevational view of an example of the present invention specialty garment accessory illustrating one of the magnetic microphones retained on a side of a person's head and a power cord from the magnetic microphone extending through a corresponding loop retained on an inner side of the specialty garment accessory and adjacent to the open collar of the specialty garment accessory.
Figure 5:
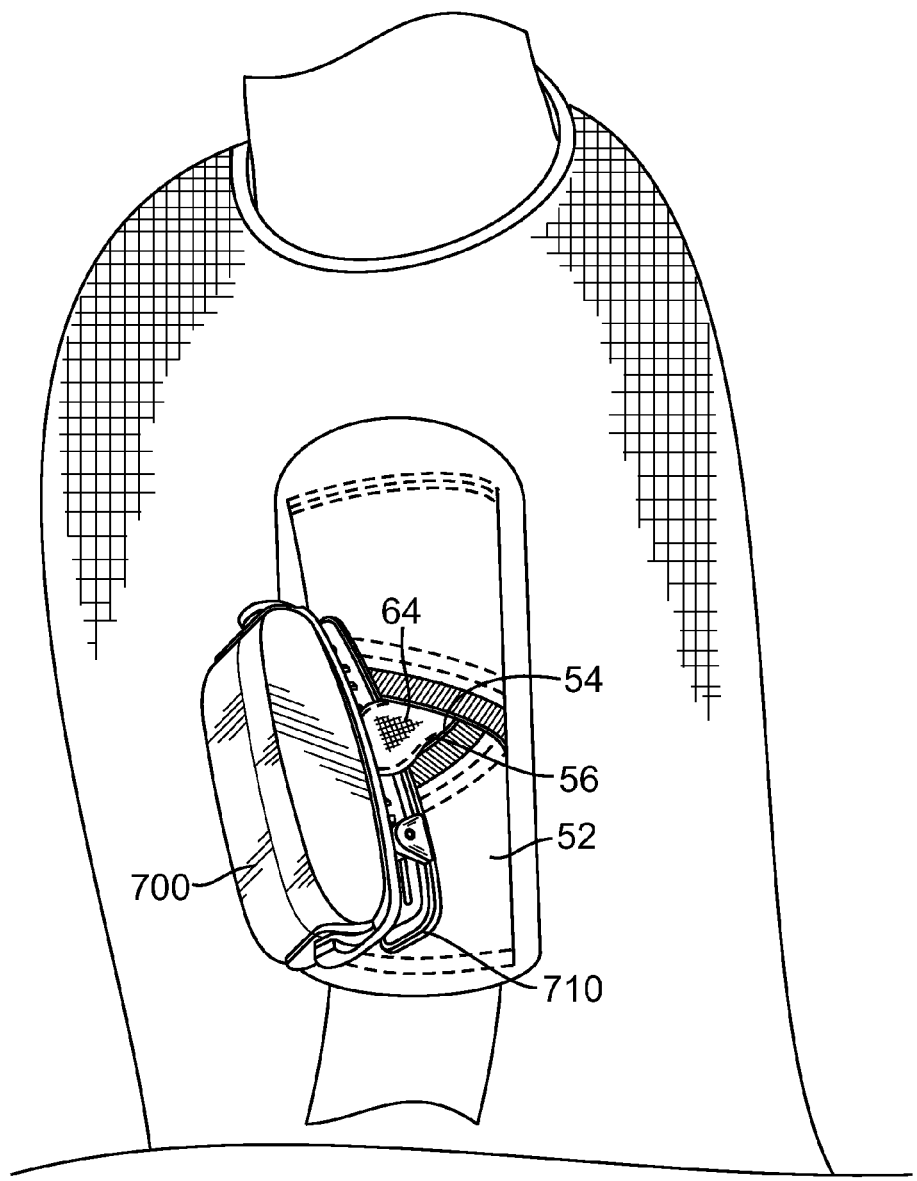
FIG. 5 is a side elevational view of a first driver unit/sound process retained in a first pocket on a left sleeve of the specialty garment accessory.
Figure 6:
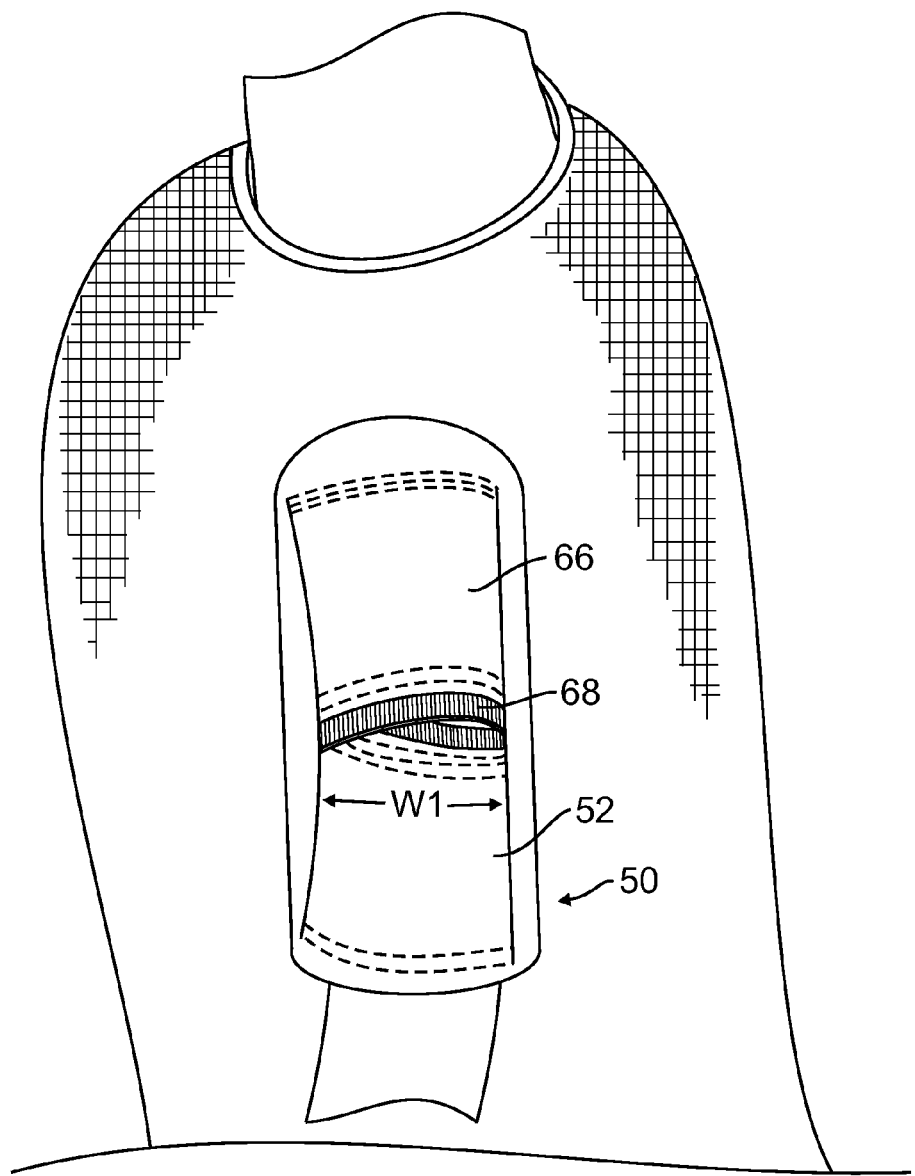
FIG. 6 is a side elevational view of the first driver unit/sound processor in the first pocket of a left sleeve of the specialty garment accessory with the first pocket closed by a cover member.
Figure 7:
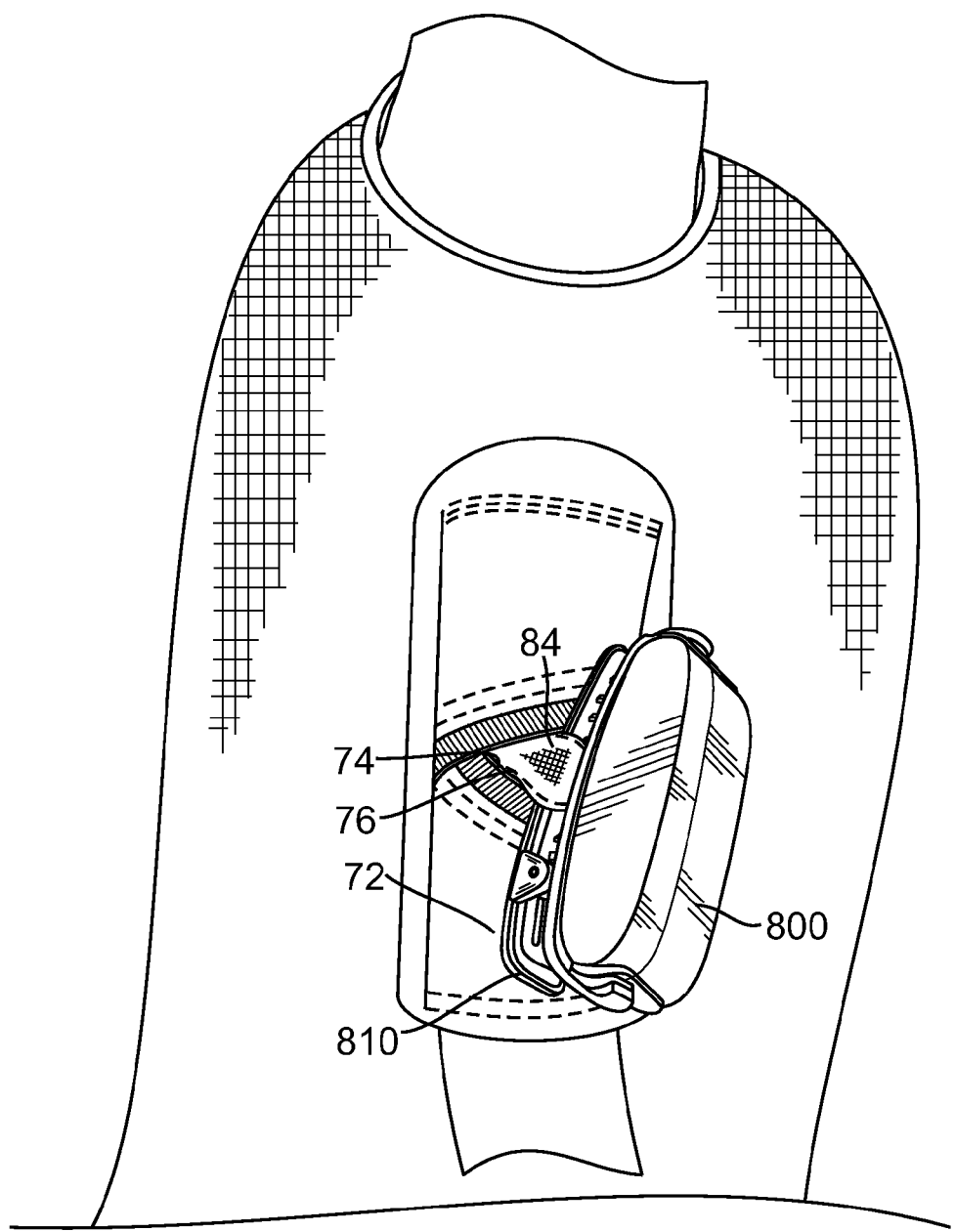
FIG. 7 is a side elevational view of a second driver unit/sound processor retained in a second pocket on a right sleeve of the specialty garment accessory.
Figure 8:
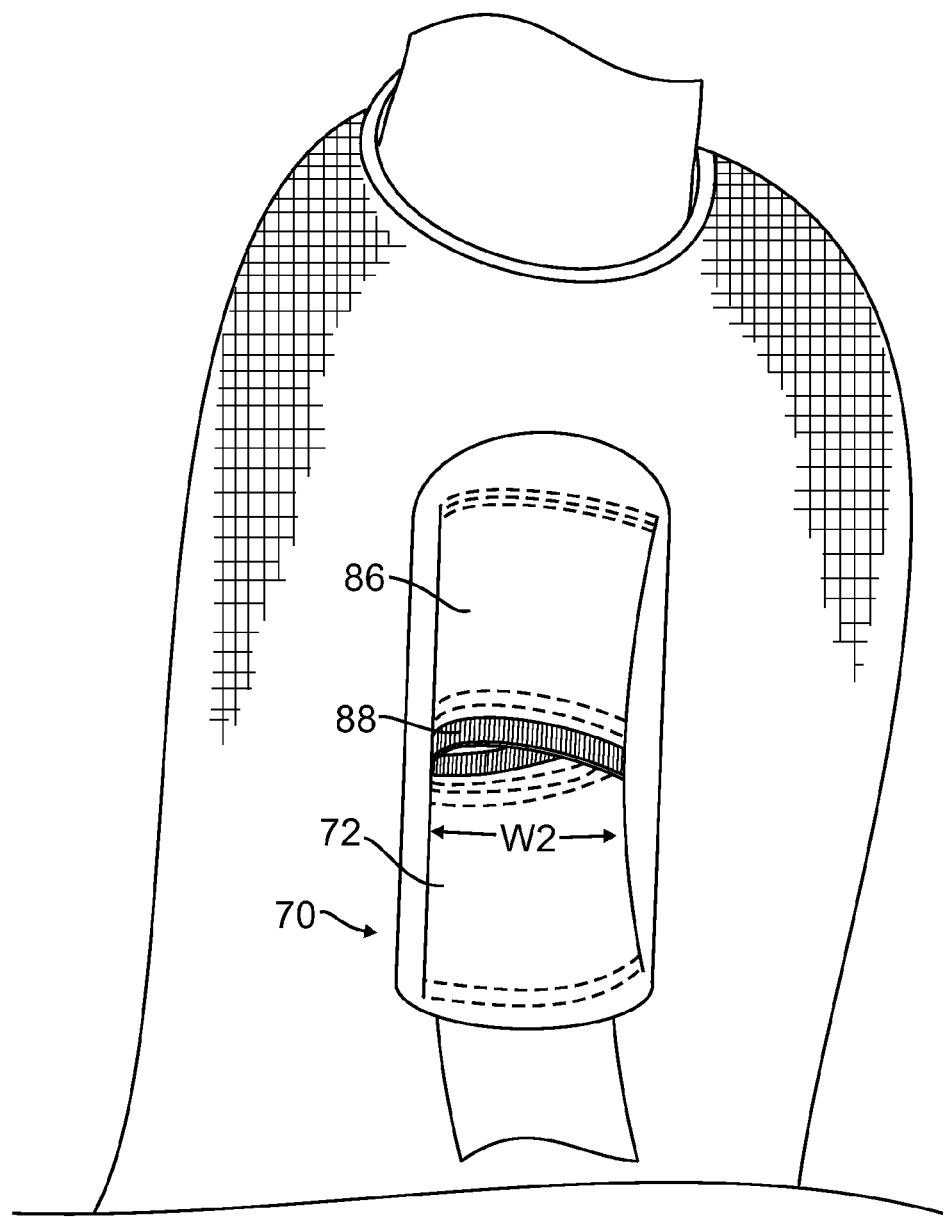
FIG. 8 is a side elevational view of the second driver unit/sound processor in the second pocket of a right sleeve of the specialty garment accessory with the second pocket closed by a cover member.

Referring to FIGS. 1 through 8, there is illustrated in FIGS. 3 and 4 the head 1100 of a person 1000 and the person's neck 1200, with an example of a specialty garment accessory of the present invention 10 worn by the person 1000 so that the person's neck 1200 extends through an open collar 30 in the body 18 of the specialty garment accessory 10 after the implant has been implanted in a person's skull as previously described. On the outside of the person's head are magnetic microphones 500 and 600 from the cochlear implant shown on either side of a person's head 1100 which are magnetically attached to a magnetic attachment in the portion of the implant that is retained within the skull (not shown). There is one magnetic microphone on either side of the head 1100 for each ear and a left ear 1300 on the person's head 1100 is illustrated in FIG. 4. It will appreciated that a second ear is located on an opposite side of the person's head 1100. Each magnetic microphone 500 and 600 has a respective sound and power cord 510 and 610 affixed at a respective proximal end 512 and 612. As will be discussed below, a respective driver unit/sound processor 700 and 800 shown in FIGS. 5 and 7 is affixed at a respective distal end 520 and 620 of a respective sound and power cord 510 and 610.

Figure 4A:
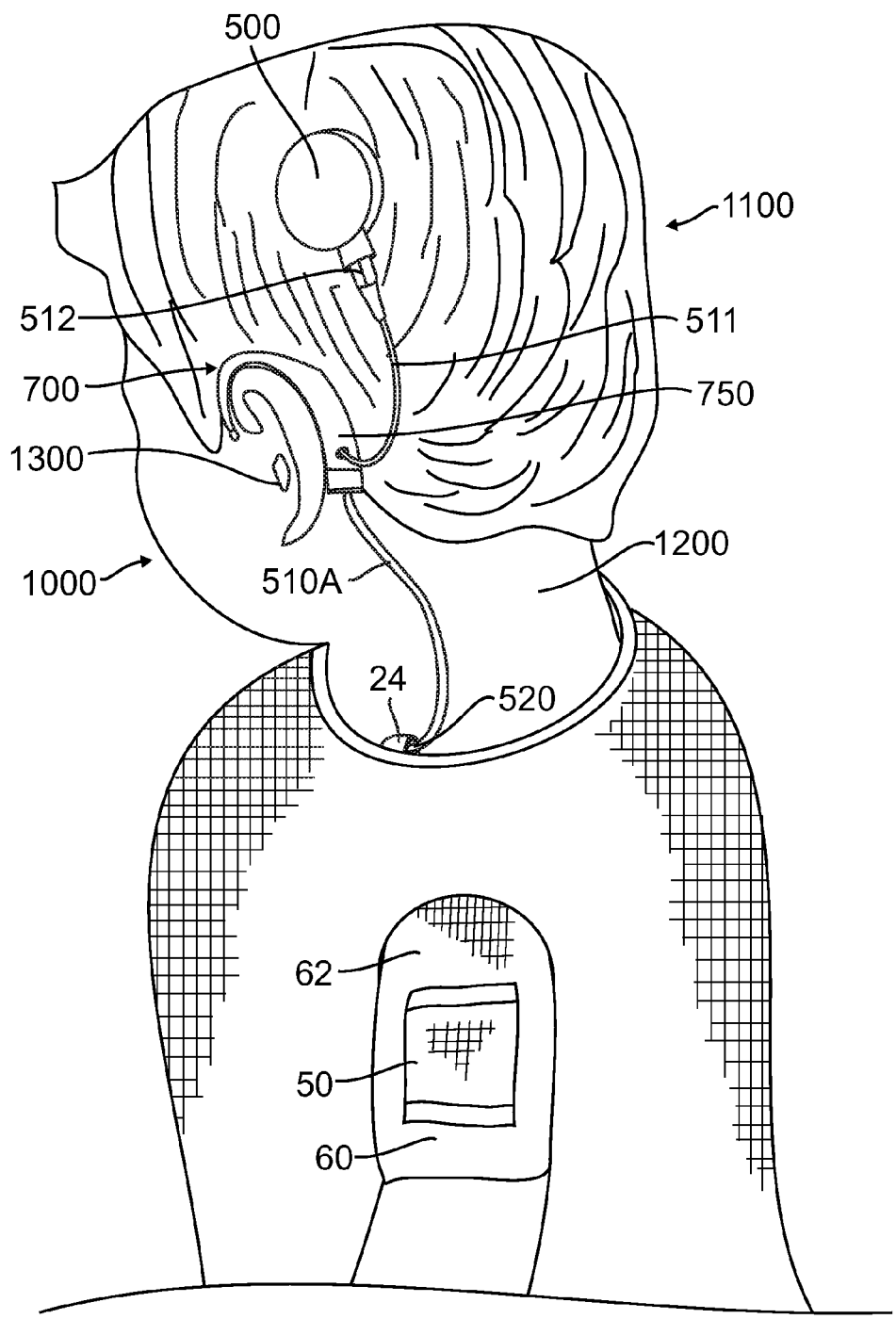
FIG. 4A is a side elevational view of an example of the present invention specialty garment accessory illustrating an alternative embodiment of one of the magnetic microphones retained on a side of a person's head and a short sound cord extending from the magnetic microphone to a sound processor retained behind the person's ear and then a power cord from the sound processor extending through a corresponding loop retained on an inner side of the specialty garment accessory and adjacent to the open collar of the specialty garment accessory.

In an alternative variation referring to FIG. 4A, the sound processor 750 is retained behind the ear and a short sound cord 511 extends from the microphone 500 to the behind the ear sound processor 750 and then a power cord 510A extends from the behind the ear sound processor to a driver unit. The configuration is the same as will be discussed with the combined unit, the only difference being that the power cord in the variation goes from the behind the ear sound processor to the driver and in the first variation, the power cord goes directly from the microphone to a combined unit which is a combined sound processor and driver.

The innovation of the present invention is having a shirt 10 (which is more generally defined as a specialty garment accessory which is selected from the group consisting of a T-shirt, sweater, sweat shirt and dress shirt) wherein sound and power cords 510 and 610 that extend from the magnetic microphones 500 and 600 on a person's head 1100 to the respective driving unit/sound processor 700 and 800 are partially concealed within the specialty garment accessory while the driving unit/sound processors 700 and 800 are concealed in a respective pocket 50 and 70 of the shirt 10 so that they are not inadvertently pulled out or damaged while the person is engaged in an activity such as swimming.

Specifically, illustrated in FIG. 1 the specialty garment accessory 10 has a body 18 terminating in an open upper neck collar 30. The outside of the body is 20 and the inside of the body is 40 shown in FIG. 2. Illustrated in FIG. 2, a first loop 24 is affixed on the inside of the body 40 adjacent the open upper neck collar 30. A second loop 28 is affixed on the inside of the body 40 adjacent the open upper neck 30 and is oppositely disposed to and generally parallel to the first loop 24. The design of the loops 24 and 28 are positioned on the collar 30 to keep the sound and power cords 510 and 610 from entanglement and the magnetic microphones 500 and 600 on the appropriate side of the head if they become dislodged. This is important since the driving unit/sound processors 700 and 800, shown in FIGS. 5 and 7, develop signals unique to their respective cochlear implant, they are not interchangeable. Additionally, the loops 24 and 28 prevent their respective magnetic microphones 500 and 600 from being pulled into the interior body 40 of shirt 10, allowing the wearer to rapidly locate an appropriate sound and power cord 510 or 610 and their respective magnetic microphone 500 or 600 to be attached to their respective internal processor. Referring back to FIG. 1, a first pocket 50 is retained on an outside section 62 of first sleeve 60, the first pocket 50 having a lower section 52 surrounding an interior chamber 54 with an opening 56 leading to the interior chamber, shown in FIG. 5. Referencing FIG. 5 and FIG. 6, a retaining member 64 such as an elastic band is affixed inside interior chamber 54 and extends across the width "W1" of the interior chamber 54. An upper covering section 66 encloses the pocket 50 with a closing member 68 such as hook and loop fasteners, snap fasteners, cover flap, a zipper, etc. enables the cover 66 to enclose the pocket 50. The first driving unit/sound process 700 is inserted through opening 56 and inserted into interior chamber 54 of first pocket 50. The first driving unit/sound processor 700 has a clip 710 by which it is clipped onto and retained by the retaining member 64 in the interior chamber 54 of first pocket 50. The retaining member 64 helps protect against loss, but it also prevents the driving unit/sound processor 700 from freely moving within the interior chamber 54 of pocket 50 during physical activity reducing the possibility of connector 518 from disconnecting from driving unit/processor 700 and wearer losing the ability to hear. The retaining member 64 can be made of any fabric material generally defined as elastic, nylon, grosgrain ribbon, etc. capable of being sewn into an ordinary garment that is strong enough to hold the driving unit/sound processor 700. The pocket 50 has an interior surface 54A and an opening 54B, referring to FIG. 2 extending through the interior surface 54A to the interior 40 of the specialty garment accessory 10. The first sound and power cord 510 extends from the first magnet microphone 500 adjacent one side of the neck, through first loop 24 and runs along the interior 40 of the specialty garment accessory so that the distal end 520 of sound and power cord 510 extends through opening 54B and is connected to the first driving unit/sound processor 700. The design of the opening 54B are specially placed in a manner to reduce tension on the distal end of power cord 520 where it connects with the driving unit/sound processor 700. Minimization of tension on connectors 520 is important since this junction may be sensitive to bending damage or becoming disconnected. Should damage or disconnection occur, the person would not be able to hear. Replacement of this power cord of a cochlear implant is expensive relative to a normal signal or power connecting wires. In this way, the sound and power cord 510 is mostly concealed within the specialty garment accessory 10 and the first driving unit/sound processor 700 is concealed within the pocket 50 while the first magnetic microphone 500 and driving unit/sound processor 700 are operational, and are protected if the person 1000 engages in physical activity such as swimming.

Further, illustrated in FIGS. 1 and 2, the specialty garment accessory 10 has a body 18 terminating in an open upper neck collar 30. The outside of the body is 20 and the inside of the body is 40. A first loop 24 is affixed on the inside of the body 40 adjacent the open upper neck collar 30. A second loop 28 is affixed on the inside of the body 40 adjacent the open upper neck 30 and is oppositely disposed to and generally parallel to the first loop 24. A second pocket 70 is retained on an outside section 82 of second sleeve 80, the second pocket 70 having a lower section 72, referring to FIGS. 7 and 8, surrounding an interior chamber 74 with an opening 76 leading to the interior chamber. A retaining member 84 such as an elastic band is affixed inside interior chamber 74 and extends across the width "W2" of the interior chamber 74. The retaining member 84 helps protect against loss, but it also prevents the driving unit/sound processor 800 from freely moving within the interior chamber 74 of pocket 70 during physical activity reducing the possibility of connector 618 from disconnecting from driving unit/processor 800 and wearer losing the ability to hear. The retaining member 84 can be made of any fabric material generally defined as elastic, nylon, grosgrain ribbon, etc. capable of being sewn into an ordinary garment that is strong enough to hold the driving unit/sound processor 800. An upper covering section 86 encloses the pocket 70 with a closing member 88 such as hook and loop fasteners, snap fasteners, cover flap, a zipper, etc. enables the cover 86 to enclose the pocket 70. The second driving unit/sound process 800 is inserted through opening 76 and inserted into interior chamber 74 of second pocket 70. The second driving unit/sound processor 800 has a clip 810 by which it is clipped onto and retained by the retaining member 84 in the interior chamber 74 of second pocket 70. The retaining member 84 can be made of any fabric material generally defined as elastic, nylon, grosgrain ribbon, etc. capable of being sewn into an ordinary garment that is strong enough to hold the driving unit/sound processor 800. Referring to FIG. 1 and FIG. 2, the pocket 70 has an interior surface 74A and an opening 74B extending through the interior surface 74A to the interior 40 of the specialty garment accessory 10. The first sound and power cord 610 extends from the second magnet microphone 600 adjacent one side of the neck, through second loop 28 and runs along the interior 40 of the specialty garment accessory so that the distal end 620 of sound and power cord 610 extends through opening 74B and is connected to the second driving unit/sound processor 800. The design of the opening 74B are specially placed in a manner to reduce tension on the distal end of wire 620 where they connect with the driving unit/sound processor 800. Minimization of tension on connectors 618 is important since this junction may be sensitive to bending damage or becoming disconnected. Should damage or disconnection occur, the person would not be able to hear. Replacement of this power cord of a cochlear implant is expensive relative to a normal signal or power connecting cord. In this way, the sound and power cord 610 is mostly concealed within the specialty garment accessory 10 and the driving unit/sound processor is concealed within the pocket 70 while the second magnetic microphone 600 and driving unit/sound processor 800 are operational, and are protected if the person 1000 engages in physical activity such as swimming. Therefore, the innovation is to have the power cords extend through the loops within the shirt both on the interior of the shirt on either side and then extend into a pocket on the shirt wherein the driving unit/sound processor is retained with a clip attached to a transverse elastic band within the pocket so the driver unit is also concealed and protected and the wires are not exposed except for the brief location between the top of the shirt and the person's head to enable the person to actively engage in activities such as sports or swimming and at the same time enable a person to hear because of this new innovation.

In the variation that was discussed above where the sound processor is in a device behind the ear as illustrated in FIG. 4A, the specialty garment is the same but the power cords extend from the sound processor in the ear into the driving unit which is by itself but can be the same as numbered 700 and 800 but instead, is a separate driver unit which powers the device and the power cord goes from the sound processor behind the ear to the individual driver unit within the garment. There is a second shorter sound wire going from the magnetic microphone to the behind the ear sound processor. The entire description as set forth above is the same except that there is the intermediate device of the sound processor being a separate unit attached behind the ear rather than being incorporated into the driving unit but the entire assembly and system are the same with the power cord going from the sound processor to the driver unit as opposed to a power cord going from the magnetic microphone to a combined driver sound processing unit but in each case, the devices are the same and retained within a pocket, the only difference being the intermediate sound processor being behind the ear and not part of the driver unit.

While the way the invention has been illustrated is to have two separate power cords, it is within the spirit and scope of the present invention for the separate sound and power cords 510 and 610 to be looped together and go through single processor and driver unit such as 700 or 800 in one pocket or alternatively, the variation where there is a separate sound cord going to a separate behind the ear sound processor and then the power cord going from each respective sound processor, looped together and then going into the single unit which is a driver. These have not been illustrated but clearly, these are variations that are all within the spirit and scope of the present invention.

The invention is defined in detail as a specialty garment accessory to be used in conjunction with a hearing restoration device implanted on both sides of a person's human skull and bypasses the middle ear to the cochlear that stimulates the auditory nerve so that the person can hear, on the outside of the person's head are first and second magnetic microphones respectively on either side of a person's head which are respectively magnetically attached to an internal hearing restoration device that is implanted on both sides of the skull, a first wire attached at one end to the first magnetic microphone and attached at its opposite end to a first driving unit/sound processor and a second wire attached at one end to the second magnetic microphone and attached at its opposite end to a second driving unit/sound processor, comprising: (a) the specialty garment accessory having a body terminating in an open upper neck collar, the body of the specialty garment accessory having an outside and an inside, a first loop is affixed on the inside of the body adjacent the open upper neck collar, a second loop is affixed on the inside of the body adjacent the open upper neck and is oppositely disposed to and generally parallel to the first loop, a first pocket is retained on an outside section of a first sleeve of the specialty garment accessory, the first pocket having a lower section surrounding an interior chamber with an opening leading to the interior chamber of the first pocket and a first retaining member affixed inside the interior chamber and extends across a width of the interior chamber of the first pocket and an upper covering section enclosing the first pocket with a closing member which enables the cover to enclose the first pocket, the first pocket having an interior surface and an opening extending through the interior surface to the interior of the specialty garment accessory, a second pocket is retained on an outside section of a second sleeve of the specialty garment accessory, the second pocket having a lower section surrounding an interior chamber with an opening leading to the interior chamber of the second pocket and a second retaining member affixed inside the interior chamber and extends across a width of the interior chamber of the second pocket and an upper covering section enclosing the second pocket with a closing member which enables the cover to enclose the second pocket, the second pocket having an interior surface and an opening extending through the interior surface to the interior of the specialty garment accessory, (b) the first wire extends from a proximal end affixed to the first magnetic microphone adjacent one side of the head, through the first loop and runs along the interior of the specialty garment accessory so that a distal end of the first wire extends through a first opening in the interior of the specialty garment accessory and is connected to the first driving unit/sound processor which is retained in the interior chamber of the lower section of the first pocket and affixed to the first retaining member in the first pocket by a clip of the first driving unit/sound processor with the first cover covering the lower section of the first pocket and retained thereto by a first retaining member so that the first wire is mostly concealed within the specialty garment accessory and the first driving unit/sound processor is concealed within the first pocket while the first magnetic microphone and first driving unit/sound processor are operational, and are protected if the person engages in physical activity; and (c) the second wire extends from a proximal end affixed to the second magnetic microphone adjacent one side of the head, through the second loop and runs along the interior of the specialty garment accessory so that a distal end of the second wire extends through a second opening in the interior of the specialty garment accessory and is connected to the second driving unit/sound processor which is retained in the interior chamber of the lower section of the second pocket and affixed to the second retaining member in the second pocket by a clip of the second driving unit/sound processor with the second cover covering the lower section of the second pocket and retained thereto by a second retaining member so that the second wire is mostly concealed within the specialty garment accessory and the second driving unit/sound processor is concealed within the second pocket while the second magnetic microphone and second driving unit/sound processor are operational, and are protected if the person engages in physical activity;

The specialty garment accessory is selected from the group consisting of T-shirts, sweatshirts, sweaters and dress shirts.

The first retaining member can be an elastic band and the second retaining member can be an elastic band.

The invention is defined more broadly as a specialty garment accessory to be used in conjunction with a hearing restoration device which includes first and second external hearing components respectively on either side of a person's head which are respectively removably attached to respective exterior locations on opposite sides of the person's head respectively aligned with a respective hearing restoration device, a first wire attached at one end to the first external hearing component and attached at its opposite end to a first sound processor and a second wire attached at one end to the second hearing component and attached at its opposite end to a second sound processor, comprising: (a) the specialty garment accessory having a body terminating in an open upper neck collar, the body of the specialty garment accessory having an outside and an inside, a first wire guiding member affixed to the specialty garment accessory adjacent the open upper neck collar, a second wire guiding member affixed to the specialty garment accessory adjacent the open upper neck and is oppositely disposed to and generally parallel to the first wire guiding member, a first pocket is retained on an outside section of a first sleeve of the specialty garment accessory, the first pocket having a lower section surrounding an interior chamber with an opening leading to the interior chamber of the first pocket and a first retaining member affixed inside the interior chamber and extends across a width of the interior chamber of the first pocket and an upper covering section enclosing the first pocket with a closing member which enables the cover to enclose the first pocket, the first pocket having an interior surface and an opening extending through the interior surface to the interior of the specialty garment accessory, a second pocket is retained on an outside section of a second sleeve of the specialty garment accessory, the second pocket having a lower section surrounding an interior chamber with an opening leading to the interior chamber of the second pocket and a second retaining member affixed inside the interior chamber and extends across a width of the interior chamber of the second pocket and an upper covering section enclosing the second pocket with a closing member which enables the cover to enclose the second pocket, the second pocket having an interior surface and an opening extending through the interior surface to the interior of the specialty garment accessory; (b) the first wire extends from a proximal end affixed to the first external hearing component adjacent one side of the head, through the first wire guiding member and runs along the interior of the specialty garment accessory so that a distal end of the first wire extends through a first opening in the interior of the specialty garment accessory and is connected to the first sound processor which is retained in the interior chamber of the lower section of the first pocket and affixed to the retaining member in the first pocket by a first sound processor retaining member with the first cover covering the lower section of the first pocket and retained thereto by a first covering retaining member so that the first wire is mostly concealed within the specialty garment accessory and the first sound processor is concealed within the first pocket while the first external hearing component and first sound processor are operational, and are protected if the person engages in physical activity; and (c) the second wire extends from a proximal end affixed to the second external hearing component adjacent one side of the head, through the second wire guiding member and runs along the interior of the specialty garment accessory so that a distal end of the second wire extends through a second opening in the interior of the specialty garment accessory and is connected to the second sound processor which is retained in the interior chamber of the lower section of the second pocket and affixed to the retaining member in the second pocket by a second sound processor retaining member with the second cover covering the lower section of the second pocket and retained thereto by a second covering retaining member so that the second wire is mostly concealed within the specialty garment accessory and the second sound processor is concealed within the second pocket while the second external hearing component and second sound processor are operational, and are protected if the person engages in physical activity.

The invention is defined most broadly as a specialty garment accessory to be used in conjunction with a hearing restoration device implanted on at least one side of a person's human skull and goes to an inner ear bypassing the middle ear to the auditory nerve so that the person can hear, on the outside of the person's head are at least a first magnetic microphone on a side of a person's head which is respectively magnetically attached to a magnetic attachment which is part of the hearing restoration device that is implanted within and on at least one side of the skull, a wire attached at one end to the at least one magnetic microphone and attached at its opposite end to at least one driving unit/sound processor, comprising: (a) the specialty garment accessory having a body terminating in an open upper neck collar, the body of the specialty garment accessory having an outside and an inside, at least one loop is affixed on the inside of the body adjacent the open upper neck collar, at least one pocket is retained on an outside section of a first sleeve of the specialty garment accessory, the at least one pocket having a lower section surrounding an interior chamber with an opening leading to the interior chamber of the at least one pocket and a retaining member affixed inside the interior chamber and extends across a width of the interior chamber of the at least one pocket and an upper covering section enclosing the at least one pocket with a closing member which enables the cover to enclose the at least one pocket, the at least one pocket having an interior surface and an opening extending through the interior surface to the interior of the specialty garment accessory; and (b) the at least one wire extends from a proximal end affixed to the at least one magnetic microphone adjacent one side of the head, through the at least one loop and runs along the interior of the specialty garment accessory so that a distal end of the at least one wire extends through the opening in the interior of the specialty garment accessory and is connected to the at least one driving unit/sound processor which is retained in the interior chamber of the lower section of the at least one pocket and affixed to the retaining member in the at least one pocket by a clip of the at least one driving unit/sound processor with the cover covering the lower section of the at least one pocket and retained thereto by the retaining member so that the wire is mostly concealed within the specialty garment accessory and the at least one driving unit/sound processor is concealed within the at least one pocket while the at least one magnetic microphone and at least one driving unit/sound processor are operational, and are protected if the person engages in physical activity.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A specialty garment accessory to be used in conjunction with a pair of cochlear implants respectively implanted into a respective cochlea in a respective side of a person's human skull and bypasses the middle ear to the cochlea that stimulates the auditory nerve so that the person can hear, on the outside of the person's head are first and second magnetic microphones respectively on either side of a person's head which are respectively magnetically attached to an internal hearing restoration device that is implanted on both sides of the skull, a first sound and power cord attached at one end to the first magnetic microphone and attached at its opposite end to a first driving unit/sound processor and a second sound and power cord attached at one end to the second magnetic microphone and attached at its opposite end to a second driving unit/sound processor, the accessory comprising:

a. a specialty garment accessory having a body terminating in an open upper neck collar having an enclosed circumferential opening, the body of the specialty garment accessory having an outside and an inside, a first loop affixed on the inside of the body adjacent the open upper neck collar, a second loop affixed on the inside of the body adjacent the open upper neck collar and is oppositely disposed to and generally parallel to the first loop, a first pocket retained on an outside section of a first sleeve of the specialty garment accessory, the first pocket having a lower section surrounding an interior chamber with an opening leading to the interior chamber of the first pocket and a first retaining member affixed inside the interior chamber and extends across a width of the interior chamber of the first pocket and an upper covering section enclosing the first pocket with a closing member which enables the cover to enclose the first pocket, the first pocket having an interior surface and an opening extending through the interior surface to the interior of the specialty garment accessory, a second pocket retained on an outside section of a second sleeve of the specialty garment accessory, the second pocket having a lower section surrounding an interior chamber with an opening leading to the interior chamber of the second pocket and a second retaining member affixed inside the interior chamber and extends across a width of the interior chamber of the second pocket and an upper covering section enclosing the second pocket with a closing member which enables the cover to enclose the second pocket, the second pocket having an interior surface and an opening extending through the interior surface to the interior of the specialty garment accessory;

b. the first sound and power cord extending from a proximal end affixed to the first magnetic microphone through the first loop and extending along the interior of the specialty garment accessory so that a distal end of the first sound and power cord extends through a first opening in the interior surface of the first pocket of the specialty garment accessory and is connected to the first driving unit/sound processor which is retained in the interior chamber of the lower section of the first pocket and affixed to the first retaining member in the first pocket by a clip of the first driving unit/sound processor with the first cover covering the lower section of the first pocket and retained thereto by a first retaining member so that the first sound and power cord is mostly concealed within the specialty garment accessory and the first driving unit/sound processor is concealed with a first water proof connection within the first pocket while the first magnetic microphone and first driving unit/sound processor are operational, and are protected from water damage if the person engages in swimming; and c. the second sound and power cord extending from a proximal end affixed to the second magnetic microphone extending through the second loop and extending along the interior surface of the second pocket of the specialty garment accessory so that a distal end of the second sound and power cord extends through a second opening in the interior surface of the second pocket of the specialty garment accessory and is connected to the second driving unit/sound processor which is retained in the interior chamber of the lower section of the second pocket and affixed to the second retaining member in the second pocket by a clip of the second driving unit/sound processor with the second cover covering the lower section of the second pocket and retained thereto by a second retaining member so that the second sound and power cord is mostly concealed within the specialty garment accessory and the second driving unit/sound processor is concealed with a water proof connection within the second pocket while the second magnetic microphone and second driving unit/sound processor are operational, and are protected from water damage if the person engages in swimming;

d. whereby the first loop affixed on the inside of the body adjacent to the upper neck collar is sized so that the first magnetic microphone will not fall out of the first loop if the first magnetic microphone is dislodged and the second loop affixed on the inside of the body adjacent to the upper neck collar is sized so that the second magnetic microphone will not fall out of the second loop if the second magnetic microphone is dislodged and the first sound and power cord will not cross the second sound and power cord when the specialty garment accessory is used in water.

2. The specialty garment accessory in accordance with claim 1, further comprising: the specialty garment accessory is selected from the group consisting of T-shirts, sweatshirts, sweaters and dress shirts.

3. The specialty garment accessory in accordance with claim 1, further comprising:
   a. the first retaining member is an elastic band; and
   b. the second retaining member is an elastic band.

4. A specialty garment accessory to be used in conjunction with a pair of cochlear implants which includes first and second external hearing components respectively on either side of a person's head which are respectively removably attached to respective exterior locations on opposite sides of the person's head respectively aligned with a respective hearing restoration device, a first power cord attached at one end to the first external hearing component and attached at its opposite end to a first sound processor and a second power cord attached at one end to the second hearing component and attached at its opposite end to a second sound processor, comprising:

a. the specialty garment accessory having a body terminating in an open upper neck collar having an enclosed circumferential opening, the body of the specialty garment accessory having an outside and an inside, a first power cord guiding member affixed to the specialty garment accessory adjacent the open upper neck collar, a second power cord guiding member affixed to the specialty garment accessory adjacent the open upper neck and oppositely disposed to and generally parallel to the first power cord guiding member, a first pocket is retained on an outside section of a first sleeve of the specialty garment accessory, the first pocket having a lower section surrounding an interior chamber with an opening leading to the interior chamber of the first pocket and a first retaining member affixed inside the interior chamber and extending across a width of the interior chamber of the first pocket and an upper covering section enclosing the first pocket with a closing member which enables the cover to enclose the first pocket, the first pocket having an interior surface and an opening extending through the interior surface to the interior of the specialty garment accessory, a second pocket retained on an outside section of a second sleeve of the specialty garment accessory, the second pocket having a lower section surrounding an interior chamber with an opening leading to the interior chamber of the second pocket and a second retaining member affixed inside the interior chamber and extending across a width of the interior chamber of the second pocket and an upper covering section enclosing the second pocket with a closing member which enables the cover to enclose the second pocket, the second pocket having an interior surface and an opening extending through the interior surface to the interior of the specialty garment accessory;

b. the first power cord extending from a proximal end affixed to the first external hearing component through the first power cord guiding member and extending along the interior of the specialty garment accessory so that a distal end of the first power cord extends through a first opening in the interior of the specialty garment accessory and is connected to the first sound processor which is retained in the interior chamber of the lower section of the first pocket and affixed to the retaining member in the first pocket by a first sound processor retaining member with the first cover covering the lower section of the first pocket and retained thereto by a first covering retaining member so that the first power cord is mostly concealed within the specialty garment accessory and the first sound processor is concealed with a first waterproof connection within the first pocket while the first external hearing component and first sound processor are operational, and are protected from water damage if the person engages in swimming; and c. the second power cord extends from a proximal end affixed to the second external hearing component through the second power cord guiding member and extending along the interior of the specialty garment accessory so that a distal end of the second power cord extends through a second opening in the interior of the specialty garment accessory and is connected to the second sound processor which is retained in the interior chamber of the lower section of the second pocket and affixed to the retaining member in the second pocket by a second sound processor retaining member with the second cover covering the lower section of the second pocket and retained thereto by a second covering retaining member so that the second power cord is mostly concealed within the specialty garment accessory and the second sound processor is concealed within the second pocket while the second external hearing component and second sound processor are operational, and are protected if the person engages in swimming;

whereby the first power cord guiding member adjacent to the upper neck collar is sized so that the first external hearing component will not fall out of the power cord guiding member if the first external hearing component is dislodged and the second power cord guiding member affixed adjacent the upper neck collar is sized so that the second external hearing component will not fall out of the second power cord guiding member if the second external hearing component is dislodged, and the first power cord and the second power cord will not cross when the specialty garment accessory is use in water.

5. The specialty garment accessory in accordance with claim 4, further comprising: the specialty garment accessory is selected from the group consisting of T-shirts, sweatshirts, sweaters and dress shirts.

6. The specialty garment accessory in accordance with claim 4, further comprising:

a. the first retaining member is an elastic band; and b. the second retaining member is an elastic band.

7. A specialty garment accessory to be used in conjunction with at least one cochlear implant implanted on at least one cochlea in a side of a person's human skull and goes to an inner ear bypassing the middle ear to the auditory nerve so that the person can hear, on the outside of the person's head are at least a first magnetic microphone on a side of a person's head which is respectively magnetically attached to a magnetic attachment which is part of the hearing restoration device that is implanted within and on at least one side of the skull, a sound and power cord attached at one end to the at least one magnetic microphone and attached at its opposite end to at least one driving unit/sound processor, comprising:

a. the specialty garment accessory having a body terminating in an open upper neck collar having an enclosed circumferential opening the body of the specialty garment accessory having an outside and an inside, at least one loop is affixed on the inside of the body adjacent the open upper neck collar, at least one pocket is retained on an outside section of a first sleeve of the specialty garment accessory, the at least one pocket having a lower section surrounding an interior chamber with an opening leading to the interior chamber of the at least one pocket and a retaining member affixed inside the interior chamber and extends across a width of the interior chamber of the at least one pocket and an upper covering section enclosing the at least one pocket with a closing member which enables the cover to enclose the at least one pocket, the at least one pocket having an interior surface and an opening extending through the interior surface to the interior of the specialty garment accessory, and b. the at least one sound and power cord extends from a proximal end affixed to the at least one magnetic microphone adjacent one side of the head, through the at least one loop and runs along the interior of the specialty garment accessory so that a distal end of the at least one sound and power cord extends through the opening in the interior of the specialty garment accessory and is connected to the at least one driving unit/sound processor which is retained in the interior chamber of the lower section of the at least one pocket and affixed to the retaining member in the at least one pocket by a clip of the at least one driving unit/sound processor with the cover covering the lower section of the at least one pocket and retained thereto by the retaining member so that the at least one sound and power cord is mostly concealed within the specialty garment accessory and the at least one driving unit/sound processor is concealed with a first waterproof connection within the at least one pocket while the at least one magnetic microphone and at least one driving unit/sound processor are operational, and are protected if the person engages in swimming.

8. The specialty garment accessory in accordance with claim 7, further comprising: the specialty garment accessory is selected from the group consisting of T-shirts, sweatshirts, sweaters and dress shirts.

9. The specialty garment accessory in accordance with claim 7, further comprising:
  a. the first retaining member is an elastic band; and
  b. the second retaining member is an elastic band.

\* \* \* \* \*